US006482348B1

(12) United States Patent
Wang et al.

(10) Patent No.: US 6,482,348 B1
(45) Date of Patent: *Nov. 19, 2002

(54) METHOD OF FORMING A CO-EXTRUDED BALLOON FOR MEDICAL PURPOSES

(75) Inventors: James C. Wang, Norton, MA (US); John Abele, Concord, MA (US); George T. Roberts, Weston, MA (US); Brian A. Pederson, Sr., South Attleboro, MA (US)

(73) Assignee: Boston Scientific Corporation, Natick, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/542,080

(22) Filed: Apr. 3, 2000

Related U.S. Application Data

(60) Continuation of application No. 08/427,997, filed on Apr. 24, 1995, now Pat. No. 6,136,258, which is a continuation of application No. 08/013,340, filed on Feb. 4, 1993, now abandoned, which is a division of application No. 07/691,999, filed on Apr. 26, 1991, now Pat. No. 5,195,969.

(51) Int. Cl.$^7$ ............................................. B29C 49/22
(52) U.S. Cl. ................... 264/514; 264/521; 264/515; 604/96; 604/194
(58) Field of Search ............................ 264/514, 521, 264/573, 510, 515; 604/96, 194

(56) References Cited

U.S. PATENT DOCUMENTS

| | | |
|---|---|---|
| 1,643,289 A | 9/1927 | Peglay |
| 1,690,995 A | 11/1928 | Pratt |
| 2,499,045 A | 2/1950 | Walker et al. ............... 128/261 |
| 2,548,602 A | 4/1951 | Greenburg ..................... 128/4 |
| 2,616,429 A | 11/1952 | Merenlender ............... 128/350 |
| 2,688,329 A | 9/1954 | Wallace ....................... 128/349 |

(List continued on next page.)

FOREIGN PATENT DOCUMENTS

| | | |
|---|---|---|
| DE | 28 48 854 A1 | 5/1979 |
| DE | 36 38 828 A1 | 5/1988 |
| DE | 31 24 198 A1 | 4/1992 |
| EP | 0 101 216 A2 | 2/1984 |
| EP | 0 166 998 | 1/1986 |
| EP | 0 174 206 A2 | 3/1986 |
| EP | 0 201 331 A2 | 11/1986 |

(List continued on next page.)

OTHER PUBLICATIONS

Article from Design Ovine Hoestche Celen USC, pp. 2–2, 3–1–3–4, 1991.

(List continued on next page.)

*Primary Examiner*—Suzanne E. McDowell
(74) *Attorney, Agent, or Firm*—Fish & Richardson P.C.

(57) ABSTRACT

A method of forming a balloon for medical purposes comprising co-extruding in a tubular shape a base structural layer of a member selected from the group consisting oft polyamides, polycarbonates, polyesters and copolymers thereof and a heat sealable layer selected from the group consisting of polyethylene and copolymers thereof. The tubular member is then biaxially oriented by inflating the tube with a gas to a predetermined central diameter greater then the initial diameter of the tube and simultaneously heating the inflated tube to a temperature sufficient to biaxially orient the base structural layer. The member is then cooled the inflated tubular member and then elevated in temperature for a second time to the biaxially orienting temperature. The twice-heated tube is allowed to cool and the gas is withdrawn whereby the tubular member will assume a generally tubular shape and the main structural layer will remain biaxially orientated and the heat sealable layer will not be biaxially orientated.

1 Claim, 1 Drawing Sheet

U.S. PATENT DOCUMENTS

| | | | |
|---|---|---|---|
| 2,690,595 A | 10/1954 | Raiche | 18/59.7 |
| 2,799,273 A | 7/1957 | Oddo | 128/325 |
| 2,823,421 A | 2/1958 | Scarlett | 18/57 |
| 2,936,760 A | 5/1960 | Gants | 128/349 |
| 2,981,254 A | 4/1961 | Vanderbilt | 128/350 |
| 3,045,677 A | 7/1962 | Wallace | 128/349 |
| 3,053,257 A | 9/1962 | Birtwell | 128/349 |
| 3,141,912 A | 7/1964 | Goldman et al. | 264/95 |
| 3,173,418 A | 3/1965 | Baran | 128/351 |
| 3,292,627 A | 12/1966 | Harautuneian | 128/349 |
| 3,304,353 A | 2/1967 | Harautuneian | 264/98 |
| 3,348,542 A | 10/1967 | Jackson | 128/184 |
| 3,426,744 A | 2/1969 | Ball | 128/1 |
| 3,432,591 A | 3/1969 | Heffelfinger | 264/289 |
| 3,539,674 A | 11/1970 | Dereniuk et al. | 264/130 |
| 3,543,758 A | 12/1970 | McWhorter | 128/349 |
| 3,543,759 A | 12/1970 | McWhorter | 128/349 |
| 3,561,493 A | 2/1971 | Maillard | 138/141 |
| 3,562,352 A | 2/1971 | Nyilas | 260/824 |
| 3,618,614 A | 11/1971 | Flynn | 128/348 |
| 3,707,146 A | 12/1972 | Cook et al. | 128/2 R |
| 3,707,151 A | 12/1972 | Jackson | 128/351 |
| 3,731,692 A | 5/1973 | Goodyear | 128/351 |
| 3,733,309 A | 5/1973 | Wyeth et al. | 260/75 |
| 3,745,150 A | 7/1973 | Corsover | 260/75 |
| 3,769,984 A | 11/1973 | Muench | 128/404 |
| 3,771,527 A | 11/1973 | Ruisi | 128/350 |
| 3,799,172 A | 3/1974 | Szpur | 128/349 R |
| 3,807,408 A | 4/1974 | Summers | 128/349 |
| 3,814,137 A | 6/1974 | Martinez | 138/103 |
| 3,833,004 A | 9/1974 | Vazquez et al. | 128/349 B |
| 3,837,347 A | 9/1974 | Tower | 128/404 |
| 3,861,972 A | 1/1975 | Glover et al. | 156/86 |
| 3,889,685 A | 6/1975 | Miller, Jr. et al. | 128/348 |
| 3,924,634 A | 12/1975 | Taylor et al. | 128/349 B |
| 3,959,426 A * | 5/1976 | Seefluth | 264/529 |
| 3,962,519 A | 6/1976 | Rusch et al. | 428/409 |
| 3,996,938 A | 12/1976 | Clark, III | 128/348 |
| 4,011,189 A | 3/1977 | Keil | 260/33.6 |
| 4,035,534 A | 7/1977 | Nyberg | 428/36 |
| 4,047,868 A | 9/1977 | Kudo et al. | 425/133.1 |
| 4,061,707 A | 12/1977 | Nohtomi et al. | 264/95 |
| 4,079,850 A | 3/1978 | Suzuki et al. | 215/1 C |
| 4,085,757 A | 4/1978 | Pevsner | 128/325 |
| 4,105,022 A | 8/1978 | Antoshkiw et al. | 128/2.05 |
| 4,140,126 A | 2/1979 | Choudhury | 128/325 |
| 4,141,364 A | 2/1979 | Schultze | 128/349 B |
| 4,144,298 A | 3/1979 | Lee | 264/532 |
| 4,174,783 A | 11/1979 | Abe et al. | 215/1 C |
| 4,182,457 A | 1/1980 | Yamada | 215/1 |
| 4,183,102 A | 1/1980 | Guiset | 3/1.4 |
| 4,195,637 A | 4/1980 | Gruntzig et al. | 128/348 |
| 4,198,981 A | 4/1980 | Sinnreich | 128/344 |
| 4,211,741 A | 7/1980 | Ostoich | 264/173 |
| 4,213,461 A | 7/1980 | Pevsner | 128/348 |
| 4,222,384 A | 9/1980 | Birtwell | 128/349 B |
| 4,233,022 A | 11/1980 | Brady et al. | 425/525 |
| 4,238,443 A | 12/1980 | Levy | 264/210.7 |
| 4,244,914 A | 1/1981 | Ranalli et al. | 264/515 |
| 4,251,305 A * | 2/1981 | Becker et al. | 156/86 |
| 4,256,789 A | 3/1981 | Suzuki et al. | 428/35 |
| 4,261,339 A | 4/1981 | Hanson et al. | 128/1 D |
| 4,263,188 A | 4/1981 | Hampton et al. | 260/29.2 |
| 4,265,276 A | 5/1981 | Hatada et al. | 138/177 |
| 4,265,848 A | 5/1981 | Rusch | 264/130 |
| 4,271,839 A | 6/1981 | Fogarty et al. | 128/344 |
| 4,282,876 A | 8/1981 | Flynn | 128/349 |
| 4,292,974 A | 10/1981 | Fogarty et al. | 128/344 |
| 4,296,156 A | 10/1981 | Lustig et al. | 428/35 |
| 4,299,226 A | 11/1981 | Banka | 128/344 |
| 4,300,550 A | 11/1981 | Gandi et al. | 128/207.18 |
| 4,301,053 A | 11/1981 | Wolfrey | 260/29.2 |
| 4,306,998 A | 12/1981 | Wenzel et al. | 260/13 |
| 4,318,947 A | 3/1982 | Joung | 428/36 |
| 4,323,071 A | 4/1982 | Simpson et al. | 128/343 |
| 4,324,262 A | 4/1982 | Hall | 128/756 |
| 4,326,532 A | 4/1982 | Hammar | 128/349 R |
| 4,327,736 A | 5/1982 | Inoue | 128/349 B |
| 4,330,497 A | 5/1982 | Agdanowski | 264/150 |
| 4,335,723 A | 6/1982 | Patel | |
| 4,338,942 A | 7/1982 | Fogarty | 128/344 |
| 4,346,698 A | 8/1982 | Hanson et al. | 128/1 D |
| 4,351,341 A | 9/1982 | Goldberg et al. | 128/348 |
| 4,378,803 A | 4/1983 | Takagi et al. | 604/280 |
| 4,385,089 A * | 5/1983 | Bonnebat et al. | 428/35 |
| 4,403,612 A | 9/1983 | Fogarty | 128/344 |
| 4,406,656 A | 9/1983 | Hattler et al. | 604/280 |
| 4,411,055 A | 10/1983 | Simpson et al. | 29/447 |
| 4,413,989 A | 11/1983 | Schjeldahl et al. | 604/96 |
| 4,417,576 A | 11/1983 | Baran | 128/207.15 |
| 4,422,447 A | 12/1983 | Schiff | 128/1 D |
| 4,423,725 A | 1/1984 | Baran et al. | 128/207.15 |
| 4,424,242 A | 1/1984 | Barbee | 428/35 |
| 4,434,797 A | 3/1984 | Silander | 128/343 |
| 4,439,394 A | 3/1984 | Appleyard | 264/535 |
| 4,444,188 A | 4/1984 | Bazell et al. | 128/348.1 |
| 4,451,256 A | 5/1984 | Weikl et al. | 128/325 |
| 4,456,011 A | 6/1984 | Warnecke | 128/325 |
| 4,472,129 A | 9/1984 | Siard | 425/381 |
| 4,479,497 A | 10/1984 | Fogarty et al. | 128/344 |
| 4,484,971 A * | 11/1984 | Wang | 156/244.14 |
| 4,490,421 A * | 12/1984 | Levy | 604/96 |
| 4,497,074 A | 2/1985 | Rey et al. | 3/1 |
| 4,521,564 A | 6/1985 | Solomon et al. | 525/54.1 |
| 4,531,997 A | 7/1985 | Johnston | 156/498 |
| 4,540,404 A | 9/1985 | Wolvek | 604/96 |
| 4,551,292 A | 11/1985 | Fletcher et al. | 264/139 |
| 4,553,545 A | 11/1985 | Maass et al. | 128/341 |
| 4,559,951 A | 12/1985 | Dahl et al. | 128/642 |
| 4,572,186 A | 2/1986 | Gould et al. | 128/341 |
| 4,573,470 A | 3/1986 | Samson et al. | 128/344 |
| 4,573,966 A | 3/1986 | Weikl et al. | 604/53 |
| 4,576,142 A | 3/1986 | Schiff | 128/1 D |
| 4,576,772 A | 3/1986 | Carpenter | 264/154 |
| 4,578,024 A | 3/1986 | Sicka et al. | 425/114 |
| 4,579,879 A | 4/1986 | Flynn | 523/112 |
| 4,581,390 A | 4/1986 | Flynn | 523/112 |
| 4,582,762 A | 4/1986 | Onohara et al. | 428/447 |
| 4,585,000 A | 4/1986 | Hershenson | 128/345 |
| 4,596,563 A * | 6/1986 | Pande | 264/173 |
| 4,606,347 A | 8/1986 | Fogarty et al. | 128/344 |
| 4,608,984 A | 9/1986 | Fogarty | 128/344 |
| 4,610,662 A | 9/1986 | Weikl et al. | 604/53 |
| 4,613,517 A | 9/1986 | Williams et al. | 427/2 |
| 4,614,188 A | 9/1986 | Bazell et al. | 128/348.1 |
| 4,627,436 A | 12/1986 | Leckrone | 128/303.1 |
| 4,627,844 A | 12/1986 | Schmitt | 604/264 |
| 4,634,615 A | 1/1987 | Versteegh et al. | 428/36 |
| 4,636,346 A | 1/1987 | Gold et al. | 264/139 |
| 4,636,442 A | 1/1987 | Beavers et al. | 428/480 |
| 4,637,396 A | 1/1987 | Cook | 128/344 |
| 4,638,805 A | 1/1987 | Powell | 128/344 |
| 4,640,852 A | 2/1987 | Ossian | 428/35 |
| 4,642,267 A | 2/1987 | Creasy et al. | 428/413 |
| 4,648,871 A | 3/1987 | Jacob | 604/149 |
| 4,650,466 A | 3/1987 | Luther | 604/95 |
| 4,651,721 A | 3/1987 | Mikulich et al. | 128/79 |
| 4,655,745 A | 4/1987 | Corbett | 604/49 |
| 4,655,771 A | 4/1987 | Wallsten | 623/1 |
| 4,656,070 A | 4/1987 | Nyberg et al. | 428/36 |
| 4,657,024 A | 4/1987 | Coneys | 128/658 |

| | | | | | | |
|---|---|---|---|---|---|---|
| 4,660,560 A | 4/1987 | Klein .................. 128/344 | 4,906,244 A | 3/1990 | Pinchuk et al. ............. 606/194 |
| 4,664,657 A | 5/1987 | Williamitis et al. ......... 604/265 | 4,909,252 A | 3/1990 | Goldberger ................. 606/194 |
| 4,666,437 A | 5/1987 | Lambert .................. 604/265 | 4,913,701 A | 4/1990 | Tower .................. 604/103 |
| 4,677,017 A | 6/1987 | DeAntonis et al. ......... 428/214 | 4,921,479 A | 5/1990 | Grayzel .................. 604/53 |
| 4,681,564 A | 7/1987 | Landreneau .................. 604/97 | 4,921,483 A | 5/1990 | Wijay et al. .................. 604/96 |
| 4,684,363 A | 8/1987 | Ari et al. .................. 604/98 | 4,923,450 A | 5/1990 | Maeda et al. .................. 604/265 |
| 4,685,447 A | 8/1987 | Iversen et al. .................. 128/1 R | 4,932,956 A | 6/1990 | Reddy et al. .................. 606/192 |
| 4,685,458 A | 8/1987 | Leckrone .................. 128/303.1 | 4,932,958 A | 6/1990 | Reddy et al. .................. 606/192 |
| 4,686,124 A | 8/1987 | Onohara et al. .................. 428/35 | 4,933,178 A | 6/1990 | Capelli .................. 424/78 |
| 4,693,243 A | 9/1987 | Buras .................. 128/207.15 | 4,934,999 A | 6/1990 | Bader .................. 600/29 |
| 4,699,611 A | 10/1987 | Bowden .................. 604/51 | 4,938,676 A * | 7/1990 | Jackowski .................. 264/530 |
| 4,702,252 A | 10/1987 | Brooks et al. .................. 128/344 | 4,941,877 A | 7/1990 | Montano, Jr. .................. 604/96 |
| 4,705,502 A | 11/1987 | Patel .................. 604/49 | 4,946,464 A | 8/1990 | Pevsner .................. 606/192 |
| 4,705,517 A | 11/1987 | DiPesa, Jr. .................. 623/12 | 4,950,227 A | 8/1990 | Savin et al. .................. 604/8 |
| 4,705,709 A | 11/1987 | Vailancourt .................. 428/36 | 4,950,239 A | 8/1990 | Gahara et al. .................. 604/96 |
| 4,706,670 A | 11/1987 | Andersen et al. .................. 128/344 | 4,952,357 A | 8/1990 | Eutenuer .................. 264/129 |
| 4,710,181 A | 12/1987 | Fuqua .................. 604/265 | 4,954,126 A | 9/1990 | Wallsten .................. 600/36 |
| 4,723,936 A | 2/1988 | Buchbinder et al. .................. 604/95 | 4,960,410 A | 10/1990 | Pinchuk .................. 604/96 |
| 4,729,914 A | 3/1988 | Kliment et al. .................. 428/36 | 4,963,306 A | 10/1990 | Weldon .................. 264/101 |
| 4,732,152 A | 3/1988 | Wallsten et al. .................. 128/343 | 4,963,313 A | 10/1990 | Noddin et al. .................. 264/573 |
| 4,737,219 A | 4/1988 | Taller et al. .................. 156/215 | 4,964,853 A | 10/1990 | Sugiyama et al. .................. 604/96 |
| 4,743,257 A | 5/1988 | Tormala et al. .................. 623/16 | 4,973,301 A | 11/1990 | Nissenkorn .................. 604/8 |
| 4,744,366 A | 5/1988 | Jang .................. 128/344 | 4,986,830 A | 1/1991 | Owens et al. .................. 606/194 |
| 4,751,924 A | 6/1988 | Hammerschmidt et al. .................. 128/207.15 | 4,994,033 A | 2/1991 | Shockey et al. .................. 604/101 |
| | | | 4,994,047 A | 2/1991 | Walker et al. .................. 606/264 |
| 4,753,765 A | 6/1988 | Pande .................. 264/149 | 4,994,072 A | 2/1991 | Bhate et al. .................. 606/194 |
| 4,762,129 A | 8/1988 | Bonzel .................. 128/344 | 4,995,868 A | 2/1991 | Brazier .................. 604/105 |
| 4,762,130 A | 8/1988 | Fogarty et al. .................. 128/348.1 | RE33,561 E | 3/1991 | Levy .................. 428/36.92 |
| 4,762,589 A | 8/1988 | Akiyama et al. .................. 156/307.3 | 5,000,734 A | 3/1991 | Boussignac et al. .................. 604/96 |
| 4,763,653 A | 8/1988 | Rockey .................. 128/344 | 5,002,531 A | 3/1991 | Bonzel .................. 604/96 |
| 4,771,776 A | 9/1988 | Powell et al. .................. 128/344 | 5,002,556 A | 3/1991 | Ishida et al. .................. 606/191 |
| 4,771,778 A | 9/1988 | Mar .................. 128/344 | 5,006,119 A | 4/1991 | Acker et al. .................. 606/27 |
| 4,775,371 A | 10/1988 | Mueller, Jr. .................. 604/208 | 5,015,231 A | 5/1991 | Keith et al. .................. 604/96 |
| 4,776,337 A | 10/1988 | Palmaz .................. 128/344 | 5,017,325 A | 5/1991 | Jackowski et al. .................. 264/521 |
| 4,786,556 A | 11/1988 | Hu et al. .................. 428/412 | 5,026,607 A | 6/1991 | Kiezulas .................. 428/423.7 |
| 4,787,388 A | 11/1988 | Hofmann .................. 128/344 | 5,035,694 A | 7/1991 | Kasprzyk et al. .................. 606/27 |
| 4,790,831 A | 12/1988 | Skribiski .................. 604/282 | 5,037,392 A | 8/1991 | Hillstead .................. 604/96 |
| 4,795,458 A | 1/1989 | Regan .................. 623/1 | 5,041,089 A | 8/1991 | Muelier et al. .................. 604/96 |
| 4,796,629 A | 1/1989 | Grayzel .................. 128/344 | 5,041,100 A | 8/1991 | Rowland et al. .................. 604/265 |
| 4,800,882 A | 1/1989 | Gianturco .................. 128/343 | 5,041,125 A | 8/1991 | Montano, Jr. .................. 606/192 |
| 4,801,297 A | 1/1989 | Mueller .................. 604/280 | 5,042,985 A | 8/1991 | Elliott et al. .................. 606/192 |
| 4,803,035 A | 2/1989 | Kresge et al. .................. 264/519 | 5,049,132 A | 9/1991 | Shaffer et al. .................. 604/101 |
| 4,807,626 A | 2/1989 | McGirr .................. 128/328 | 5,057,092 A | 10/1991 | Webster, Jr. .................. 604/282 |
| 4,810,543 A | 3/1989 | Gould et al. .................. 428/35.7 | 5,057,106 A | 10/1991 | Kasevich et al. .................. 606/33 |
| 4,811,737 A | 3/1989 | Rydell .................. 128/344 | 5,059,269 A | 10/1991 | Hu et al. .................. 156/244.11 |
| 4,814,231 A | 3/1989 | Onohara et al. .................. 428/425.5 | 5,061,424 A | 10/1991 | Karimi et al. .................. 264/171 |
| 4,816,339 A | 3/1989 | Tu et al. .................. 428/421 | 5,071,406 A | 12/1991 | Jang .................. 604/96 |
| 4,818,592 A | 4/1989 | Ossian .................. 428/216 | 5,071,686 A | 12/1991 | Genske et al. .................. 428/35.7 |
| 4,819,751 A | 4/1989 | Shimada et al. .................. 128/344 | 5,074,840 A | 12/1991 | Yoon .................. 604/15 |
| 4,820,349 A * | 4/1989 | Saab .................. 604/96 | 5,074,845 A * | 12/1991 | Miraki et al. .................. 606/194 |
| 4,821,722 A | 4/1989 | Miller et al. .................. 128/344 | 5,075,152 A | 12/1991 | Tsukuda et al. .................. 428/204 |
| 4,824,618 A | 4/1989 | Strum et al. .................. 264/37 | 5,077,352 A | 12/1991 | Elton .................. 525/409 |
| 4,834,702 A | 5/1989 | Rocco .................. 604/43 | 5,078,702 A | 1/1992 | Pomeranz .................. 604/280 |
| 4,834,721 A | 5/1989 | Onohara et al. .................. 604/266 | 5,084,315 A | 1/1992 | Karimi et al. .................. 428/36.6 |
| 4,838,876 A | 6/1989 | Wong et al. .................. 604/265 | 5,087,244 A | 2/1992 | Wolinsky et al. .................. 604/53 |
| 4,840,623 A | 6/1989 | Quackenbush .................. 604/280 | 5,087,246 A | 2/1992 | Smith .................. 604/96 |
| 4,846,812 A | 7/1989 | Walker et al. .................. 604/280 | 5,090,958 A | 2/1992 | Sahota .................. 604/98 |
| 4,856,516 A | 8/1989 | Hillstead .................. 128/343 | 5,091,205 A | 2/1992 | Fan .................. 427/2 |
| 4,857,393 A | 8/1989 | Kato et al. .................. 428/289 | 5,094,799 A * | 3/1992 | Takashige et al. .................. 264/514 |
| 4,863,426 A | 9/1989 | Ferragamo et al. .................. 604/93 | 5,100,381 A | 3/1992 | Burns .................. 604/96 |
| 4,868,044 A | 9/1989 | Tanaka et al. .................. 428/304.4 | 5,100,721 A | 3/1992 | Akao .................. 428/218 |
| 4,869,263 A | 9/1989 | Segal et al. .................. 128/692 | 5,100,992 A | 3/1992 | Cohn et al. .................. 528/26 |
| 4,871,094 A | 10/1989 | Gall et al. .................. 222/386 | 5,102,416 A | 4/1992 | Rock .................. 606/194 |
| 4,878,495 A | 11/1989 | Grayzel .................. 128/344 | 5,108,415 A | 4/1992 | Pinchuk et al. .................. 606/194 |
| 4,880,682 A | 11/1989 | Hazelton et al. .................. 428/152 | 5,108,420 A | 4/1992 | Marks .................. 606/213 |
| 4,886,062 A | 12/1989 | Wiktor .................. 128/343 | 5,114,423 A | 5/1992 | Kasprzyk et al. .................. 606/27 |
| 4,896,669 A | 1/1990 | Bhate et al. .................. 606/194 | 5,116,318 A | 5/1992 | Hillstead .................. 604/96 |
| 4,898,591 A | 2/1990 | Jang et al. .................. 604/282 | 5,125,913 A | 6/1992 | Quackenbush .................. 604/264 |
| 4,900,303 A | 2/1990 | Lemelson .................. 604/54 | 5,137,512 A | 8/1992 | Burns et al. .................. 606/96 |
| 4,906,237 A | 3/1990 | Johansson et al. .................. 604/265 | 5,147,302 A | 9/1992 | Euteneuer et al. .................. 604/103 |
| 4,906,241 A | 3/1990 | Noddin et al. .................. 606/194 | 5,156,857 A | 10/1992 | Wang et al. .................. 425/130 |

| | | | |
|---|---|---|---|
| 5,160,321 A | 11/1992 | Sahota | 604/96 |
| 5,163,949 A | 11/1992 | Bonutti | 606/192 |
| 5,171,221 A | 12/1992 | Samson | 604/96 |
| 5,176,697 A | 1/1993 | Hasson et al. | 606/191 |
| 5,179,174 A | 1/1993 | Elton | 525/409 |
| 5,183,613 A | 2/1993 | Edwards | 264/171 |
| 5,195,970 A | 3/1993 | Gahara | 604/96 |
| 5,195,972 A | 3/1993 | Inoue | 604/103 |
| 5,201,706 A | 4/1993 | Noguchi et al. | 604/96 |
| 5,209,728 A | 5/1993 | Kraus et al. | 604/96 |
| 5,223,205 A | 6/1993 | Jackowski et al. | 264/521 |
| 5,226,880 A | 7/1993 | Martin | 604/99 |
| 5,248,305 A | 9/1993 | Zdarhala | 604/280 |
| 5,254,090 A | 10/1993 | Lombardi et al. | 604/96 |
| 5,254,091 A | 10/1993 | Aliahmad et al. | 604/96 |
| 5,263,962 A | 11/1993 | Johnson et al. | 606/192 |
| 5,270,086 A * | 12/1993 | Hamlin | 428/35.2 |
| 5,272,012 A | 12/1993 | Opolski | 428/423.1 |
| 5,277,199 A | 1/1994 | DuBois et al. | 128/772 |
| 5,279,560 A | 1/1994 | Morrill et al. | 604/96 |
| 5,279,594 A | 1/1994 | Jackson | 604/265 |
| 5,290,306 A * | 3/1994 | Tretta et al. | 606/194 |
| 5,304,171 A | 4/1994 | Gregory et al. | 606/15 |
| 5,304,197 A | 4/1994 | Pinchuk | 606/194 |
| 5,306,246 A * | 4/1994 | Sahatjian et al. | 604/96 |
| 5,312,356 A | 5/1994 | Engelson et al. | 604/164 |
| 5,318,041 A | 6/1994 | DuBois et al. | 607/119 |
| 5,318,587 A | 6/1994 | Davey | 606/194 |
| 5,330,428 A * | 7/1994 | Wang et al. | 604/96 |
| 5,330,429 A | 7/1994 | Noguchi et al. | 604/96 |
| 5,334,146 A | 8/1994 | Ozasa | 604/96 |
| 5,342,307 A | 8/1994 | Euteneuer et al. | 604/103 |
| 5,344,401 A | 9/1994 | Radisch et al. | 604/96 |
| 5,358,486 A | 10/1994 | Saab | 604/96 |
| 5,364,357 A | 11/1994 | Aase | 604/96 |
| 5,366,472 A | 11/1994 | Hillstead | 606/194 |
| 5,372,603 A | 12/1994 | Acker et al. | 606/194 |
| 5,413,559 A | 5/1995 | Sirhan | 604/102 |
| 5,417,671 A | 5/1995 | Jackson | 604/265 |
| 5,509,899 A | 4/1996 | Fan et al. | 604/96 |
| 6,136,258 A * | 10/2000 | Wang et al. | 264/514 |

FOREIGN PATENT DOCUMENTS

| | | | | |
|---|---|---|---|---|
| EP | 0 214 721 A1 | 3/1987 | | |
| EP | 0 266 957 A2 | 5/1988 | | |
| EP | 274411 * | 7/1988 | | |
| EP | 0 276 908 A1 | 8/1988 | | |
| EP | 0 292 587 A1 | 11/1988 | | |
| EP | 0 303 487 A2 | 2/1989 | | |
| EP | 0 329 041 A2 | 8/1989 | | |
| EP | 0 357 562 | 3/1990 | | |
| EP | 0 358 445 A2 | 3/1990 | | |
| EP | 0 359 489 A2 | 3/1990 | | |
| EP | 0 414 350 B1 | 3/1990 | | |
| EP | 0 380 102 A1 | 8/1990 | | |
| EP | 0 383 429 | 8/1990 | | |
| EP | 0 399 712 A1 | 11/1990 | | |
| EP | 0 419 291 A1 | 3/1991 | | |
| EP | 0 420 488 A1 | 4/1991 | | |
| EP | 0 428 479 A1 | 5/1991 | | |
| EP | 0 439 202 A2 | 7/1991 | | |
| EP | 0 457 456 A1 | 11/1991 | | |
| EP | 0 461 474 A1 | 12/1991 | | |
| FR | 998035 | 1/1952 | | |
| FR | 2 328 482 | 5/1977 | | |
| GB | 693244 | 6/1953 | | |
| GB | 1533204 | 11/1978 | | |
| GB | 1556242 | 11/1979 | | |
| GB | 1600963 | 10/1981 | | |
| GB | 2 077 111 A | 12/1981 | | |
| GB | 2 078 114 A | 1/1982 | | |
| GB | 2130093 | 5/1984 | | |
| GB | 2 140 437 A | 11/1984 | | |
| GB | 2 163 386 A | 2/1986 | | |
| GB | 2 209 121 A | 5/1989 | | |
| JP | 50-75256 | * | 6/1975 | 264/515 |
| JP | 51-084877 | * | 7/1976 | 156/244.13 |
| JP | 53-042256 | * | 4/1978 | 264/514 |
| JP | 58 38778 | 3/1983 | | |
| JP | 58 188463 | 11/1983 | | |
| JP | 63-0872191 | * | 4/1988 | 264/530 |
| JP | 2 43036 | 2/1990 | | |
| JP | 3 277374 | 12/1991 | | |
| JP | 4 34590 | 2/1992 | | |
| SU | 069826 A | 1/1984 | | |
| SU | 1477423 | 5/1989 | | |
| WO | WO 84/01327 | 4/1984 | | |
| WO | WO 91/04068 | 4/1991 | | |
| WO | WO 91/17788 | 11/1991 | | |
| WO | WO 92/08512 | 5/1992 | | |
| WO | WO 92/11893 | 7/1992 | | |

OTHER PUBLICATIONS

"Extruded Tubing is Called on to Perform More Complex and Critical Surgical Jobs", Modern Plastics International, pp. 40–41, 1990.

LeMay et al., "Pinhole Balloon Rupture During Coronary Angioplasty Causing Rupture of the Coronary Artery", Catherization and Cardiovascular Diagnosis 19:91–92, 1990.

Davey, "Pleated Balloon Catheter", Biomedical Materials, Apr., 1991.

Chin et al., "Long–term Results of Intraoperative Balloon Dilatation", The Journal of Cardiovascular Surgery, 30:454–458, 1989.

Article from Plastics & Rubber Weekly, "Chemistry Advance Offers New Materials", p. 8, "One Piece Catheter", p. 8, Dec. 3, 1988.

"New Silicone–modified TPE Combined Best of Both Worlds", Biomedical Elastomers, pp. 28–30, Nov. 1988.

Article from Plastics World, "New Tie Layers Brighten Life for Coextruders", 46n, Jul. 7, 1988.

"Film Laminate Key to Record Setting Balloon Flight", Plastics Design Forum, pp. 66–68, Mar./Apr. 1988.

Mobley et al., "Effects of Organophosphorus Agents on Sarcoplasmic Reticulum in Skinned Skeletal Muscle Fibres", Toxicology and Applied Pharmacology, 94:407–413, 1988.

Carley, "A Plastics Primer", Modern Plastics Encyclopedia, pp. 4–8, 1988.

Shedd, Rader, Edenbaum et al., Willwerth et al., Gabbett, Peters, Tomanek et al., Clark, Modern Plastics Encyclopedia, pp. 93–109, 1988.

Woods, "Polyurethanes" and Torkelson "Silicones", Modern Plastics Encyclopedia, pp. 122–124, 1988.

Irwin, Belcher, Bruning and Suit, Modern Plastics Encyclopedia, pp. 203–210, 1988.

Reckner, "Testing by ASTM Methods", Modern Plastics Encyclopedia, pp. 318–320, 1988.

Wholey, "A Newly Designed Angioplasty Catheter: 'The Gemini Balloon'", CardioVascular and Interventional Radiology, 11:42–44, 1988.

"Surface Analysis of Biomedical Materials and Devices—Part 1", Biomedical Polymers, vol. 4, No. 7, pp. 1–15, 1988.

Articles from Plastics Technology, "Multi–Lumen Medical Tubing Line" and "Satellite Extruders for Coextrusion", pp. 39–41, Aug., 1987.

M–D–D–I Reports, "Polymed's One–Step Balloon Catheter Manufacturing Process," p. 15, Mar. 16, 1987.

Elastomerics, EuroNews by Maurice Botwell, "DuPont Uses New Design Concepts To Boost TP Elastomers In Europe", pp. 38–39, Nov., 1986.

Simpfendorfer et al., "Balloon Rupture During Coronary Angioplasty", Journal of Vascular Disorders, vol. 37, No. 11, pp. 828–831, Nov., 1986.

Levy, "Improved Dilation Catheter Balloons", Journal of Clinical Energy, pp. 291–296, Jul./Aug. 1986.

Article from Plastics and Rubber International, "Medical Uses Of Polymers", vol. 11, No. 3, Jun. 1986.

Jain et al., "Effect of Inflation Pressures on Coronary Angioplasty Balloons", American Journal of Cardiology, 57:26–28, Jan. 1, 1986.

Palmaz et al., "Expandable Intrahepatic Portacaval Shunt Stents: Early Experience in the Dog", AJR 145:821–825, Oct. 1985.

Palmaz et al., "Expandable Intraluminal Graft: A Preliminary Study", Radiology, vol. 156 No. 1, Jul. 1985.

Inoue, "A New Balloon Catheter for Percutaneous Transluminal Angioplasty", AJR 144:1069–1071, May 1985.

Giesy et al., "Coaxial and Linear Extrusion Balloon Catheters Compared to Guidewires . . . Urinary Tract", The Journal of Urology, vol. 133, No. 4, p. 238A, Apr. 1985.

Kinney et al., "Shear Force in Angioplasty: Its Relation to Catheter Design and Function", American Journal of Roentgenology, 144:115–122, Jan. 1985.

Letter from Modern Plastics, "Coextrusion Measurement by IR Sensors", Jun. 1984 14:8.

Giesy et al., Ureteral Access: Bypassing Impacted Stones . . . Balloon Catheter, The Journal of Urology, vol. 131, No. 4, 152A, 79th Annual Meeting of American Urological Association, Inc., May 6–10, 1984.

Giesy et al., "Coaxial Balloon Dilation and Calibration of Urethral Strictures", The American Journal of Surgery, 147:611–614, May 1984.

Fogarty et al., "Intraoperative Coronary Artery Balloon Catheter Dilatation", American Heart Journal vol. 107, No. 4, pp. 845–851, Apr., 1984.

Inoue et al., "Clinical Application of Transvenous Mitral Commissurotomy by a New Balloon Catheter", Journal of Thoracic and Cardiovascular Surgery, vol. 87, No. 3, pp. 394–402, Mar. 1984.

Kennedy et al., "Interventional Coronary Arteriography", Annual Review of Medicing: Selected Topics in the Clinical Sciences, 35:513–516, 1984.

Broad, "Plastics Revolution: A Rush of New Uses", The New York Times, Tuesday, Nov. 1, 1983.

"The Gamma Bottle", Food & Drug Packaging, vol. 47, No. 10, Oct. 1983.

"Award Caps Bottle's Introduction", USA Today, Friday, Oct. 7, 1983.

Forcinio, "Squeezable bottle ends long wait for ketchup", Food & Drug Packaging, vol. 47, No. 10, Oct. 1983.

"Rigid Plastics Are Getting a Foot in the Kitchen Door", Chemical Week, Oct. 12, 1983.

Kent et al., "Percutaneous Transluminal Coronary Angioplasty: Report From . . . Blood Institute", The American Journal of Cardiology, vol. 49, pp. 2011–2020, Jun. 1982.

Dobrin, "Balloon Embolectomy Catheters in Small Arteris, I Lateral Wall Pressures and Shear Forces", Surgery, vol. 90, No. 2, pp. 177–185, Aug. 1981.

Fogarty et al., "Adjunctive Intraoperative Arterial Dilation", Arch. Surg., 116:1381–1397, 1981.

Jekell et al., "Balloon Catheters", Acta Radiological Diagnosis, 21:47–52, 1980.

Katzen et al., "Percutaneous Transluminal Angioplasty With the Gruntzig Balloon Catheter", Arch Surg., vol. 114, No. 12, pp. 1389–1399, Jun. 1979.

Gruntzig et al., "Technique of Percutaneous Transluminal Anoplasty with the Gruntzig Balloon Catheter", American Journal of Roentgenology, vol. 132, No. 4, pp. 547–552, Apr. 1979.

Jensen, "Double–Lumen Balloon Catheter", Acta Radiological Diagnosis, 17:886–890, Nov. 1976.

Supplements to Circulation, An Official Journal of the American Heart Association, vols. 53 and 54, p. II–81, Jan.–Dec. 1976.

Radiology, vol. 115, No. 3, Jun. 1975.

Sweeting et al., "Auxiliary Film Treatments" & "Polyethylene Terephthalate Film Structure and Analysis", The Science and Technology of Polymer Films, vol. II John Wiley & Sons, Inc., pp. 639, 1971.

Adrova et al., "Polymides: A new Class of Heat–Resistant Polymers", Academy of Sciences of the USSR, Chapter 1, "Synthesis and Transformations of Polymides", pp. 1–36, 1969.

Fogarty, "The Balloon Catheter in Vascular Surgery", Review of Surgery, vol. 24, No. 1, pp. 9–19, 1967.

Encyclopedia of Polymer Science and Engineering, vol. 2, Biaxial Orientation, pp. 339–373.

Encyclopedia of Polymer Science and Engineering, vol. 2, Anionic Polymerization to Cationic Polymerization, p. 202; vol. 10, Molecular Weight . . . Polymers, pp. 619–636.

Paul, Polymer Blends, 1986.

Levy, J. Clinical Eng., 1986.

* cited by examiner

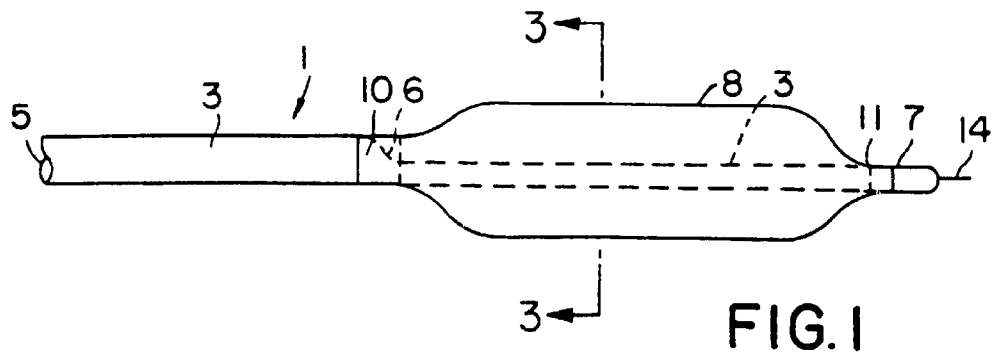
FIG. 1
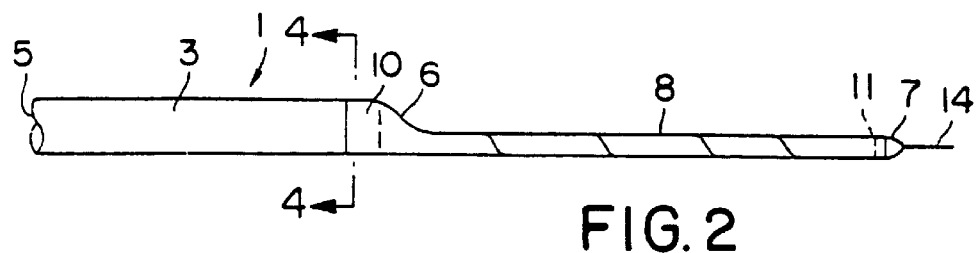
FIG. 2
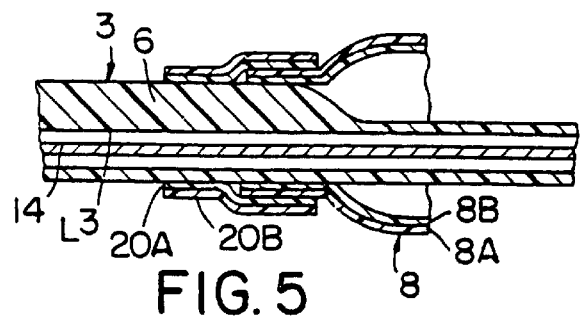
FIG. 5
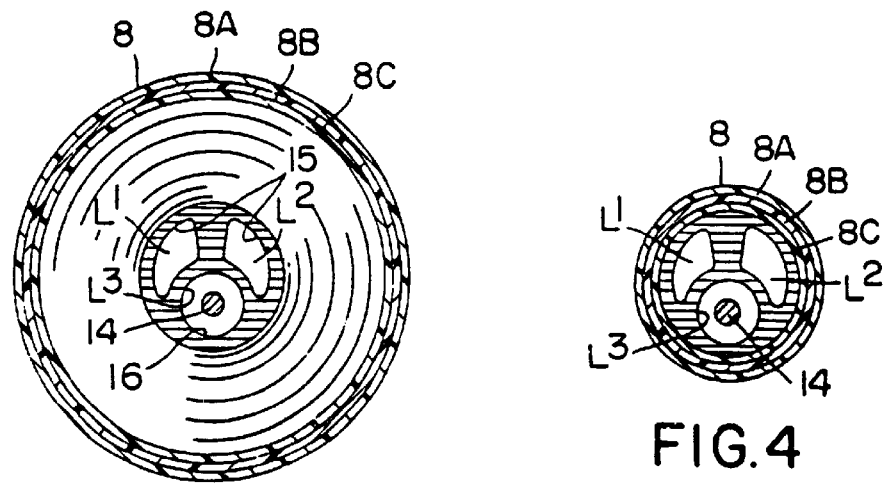
FIG. 3
FIG. 4

METHOD OF FORMING A CO-EXTRUDED BALLOON FOR MEDICAL PURPOSES

This application is a continuation of U.S. application Ser. No. 08/427,997, filed Apr. 24, 1995, now U.S. Pat. No. 6,136,258, which is a continuation of U.S. application Ser. No. 08/013,340, filed Feb. 4, 1993, now abandoned, which is a division of U.S. application, Ser. No. 07/691,999, filed Apr. 26, 1991, now U.S. Pat. No. 5,195,969.

BACKGROUND OF THE INVENTION

The present invention relates to balloons for medical devices and medical devices utilizing such balloons. More particularly, the present invention relates to medical or surgical balloons and catheters using such balloons, particularly those designed for angioplasty, valvuloplasty and urological uses and the like. The balloons of the present invention can be tailored to have expansion properties which are desired for a particular use and can be inflated to a predetermined diameter and still be resistant to the formation of pin holes and leakage.

DESCRIPTION OF THE PRIOR ART

In the past, polyethylene, polyethylene terapthalate and polyamide balloons have been used with medical catheters. Polyethylene balloons are particularly advantageous because they can be heat bonded to a like-material substrate and have a relatively low tip diameter, that is the profile of the tip at the connecting joint between the balloon and the catheter can be fairly small. Also, the polyethylene balloons are soft so that they can pass through blood vessels without trauma. Moreover, polyethylene balloons are resistant to the propagation of pin holes, primarily because the walls are thick. But since they are thick, they are large and pass by tight lesions only with great difficulty.

Balloons of polyethylene terapthalate provide low deflated profiles and can have thin walls because such materials have high tensile strengths and adequate burst strength. On the other hand, polyethylene terapthalate balloons require adhesives to bond them to the catheters and adhesive bonding frequently is not dependable and it thickens the catheter at the point of the bond. Moreover, polyethylene terapthalate can have poor pin hole resistance largely due to the very thin walls.

SUMMARY OF THE INVENTION

According to the present invention, it has been discovered that the drawbacks of the polyethylene and the polyethylene terapthalate balloons of the prior art can be remedied through the use of laminated balloon constructions which comprise a tubular body formed of a plurality of co-extruded and coextensive layers of different polymeric materials.

According to one aspect of the invention, the multi-layered balloon combines the advantages of both materials in a balloon, but does not have the disadvantages of either. The balloon includes a layer of a relatively thick, biaxially oriented ethylenic polymeric material such as polyesters, polycarbonates, polyethylene terapthalate and their copolymers, or polyamides such as Nylon. These materials constitute a base structural layer (or layers) and give the balloon its tensile strength and provide for "wear" resistance. The base structural layer may have a thickness between about 0.2 and 1.0 mil. or higher. A second layer is co-extruded with the base structural layer and is coextensive therewith. The second layer preferably is a polyolefin such as polyethylene and copolymers thereof and can be heat-bonded to a catheter, that is adhesives need not be used. The heat bondable second layer can be disposed on one and preferably both sides of the base structural layer.

In accordance with another aspect of the present invention, the base structural layer again is a material that does not itself readily thermally bond to a polyethylene catheter tubing. In those cases, sleeves of mutually bondable materials are slipped over the joints between the catheter and the balloon and the sleeves are heated to join the balloon to the sleeve and simultaneously join the sleeve to the catheter whereby to act as a fluid-tight seal between the catheter and the balloon.

With regard to multilayered balloons, the second layer (or layers) which is disposed on the base structural layer and co-extruded therewith can also serve as a barrier between the base structural layer and the environment. For example, when a polyamide such as Nylon is used as the base structural layer, a thin layer of maleic anhydride-modified ethylenic polymers such as Plexar can also be co-extruded with it. When layers are disposed on both sides of the base structural layer they keep moisture from effecting the Nylon's properties. Additional layers sometimes may also be co-extruded to bind and tie dissimilar layers together in the co-extrusion operation. When Nylon is used, for example, no tying layers are necessary between it and the heat bondable layer. In other cases, however, as when polyester or polycarbonate polymers are used as the base structural layer, adhesion enhancement may be necessary. Such adhesive enhancement may take the form of ultraviolet light irradiation of the product or the incorporation of a co-extruded tying adhesive layer.

With regard to the use of a multi-layered sleeve to join the balloon to the catheter, any conventional medical balloon material can be used that does not bond to the catheter without adhesives. The multi-layered sleeve can be formed of a base layer of the same material as the balloon with a polyethylene layer disposed on at least the inner side of the sleeve. The polyethylene will adhere to both the catheter and the balloon and form a joint with heat treatment alone.

According to the present invention, the balloons have advantages of both the polyethylene and the materials of the base structural layer. When polyethylene terapthalate is the base, very thin walls can be used with high burst strength. For example, when a typical 3.0 mm. diameter maleic anhydride-modified ethylenic polymer is coated on a Nylon base structural layer, the resulting balloon can have a wall thickness of 0.5 mil. and a low deflated profile which is comparable with polyethylene terapthalate balloons and is much lower than polyethylene balloons. When using Nylon, the material that is used is biaxially orientable and has higher tensile strength than polyethylene material, thereby resulting in a much thinner wall for comparative burst strength.

It has been found that pin hole resistance of the construction of the present invention is comparable to polyethylene and substantially superior to polyethylene terapthalate. A balloon co-extruded with Selar has superior abrasion resistance and pin hole resistance then polyethylene terapthalate balloons. Polyamide material is superior to polyethylene terapthalate and polyethylene materials in pin hole resistance. The balloon itself is soft for non-traumatic passage through blood vessels and is comparable to polyethylene because polyamide is not as stiff as polyethylene terapthalate.

In a specific embodiment of a multilayered extruded balloon, it has been found that the use of the above mentioned Selar PT resin, a trademarked compound (preferably available as Selar PT 4368 from E. I. Dupont de Nemaurs Co. of Wilmington, Del.) as a layer disposed on the base structural layer (or blended with polyethylene terapthalate) will make the balloon more resistant to abrasion and provide it with a softer feel. Selar co-extrusion in multi-layered balloons diminishes pin hole formation and will minimize failure when working with calcified lesions. Moreover, the Selar may be used as the inner layer of the balloon for use with procedures which include internal electrodes or radio-paque markers which could puncture it.

BRIEF DESCRIPTION OF THE DRAWINGS

FIG. 1 is a side elevational view of a cathete a multi-layered balloon. The balloon is shown in t. tended condition;

FIG. 2 is a view of the same catheter in the folded condition;

FIG. 3 is a cross-sectional view of the balloon of the present invention taken along the line 3—3 of FIG. 1 showing the polymeric layers in the balloon;

FIG. 4 is a cross-sectional view taken along the line 4—4 of FIG. 2 showing the balloon in its folded condition.

FIG. 5 is a cross sectional view of a distended balloon disposed at the end of a catheter and joined to the catheter by a sleeve.

DESCRIPTION OF THE PREFERRED EMBODIMENTS

An illustrative catheter 1 is shown in FIGS. 1 and 2. Catheter 1 includes a catheter tube 3 having a proximal end 5, a distal end 6 and a tip 7. A distended co-extruded medical balloon 8 of the present invention is shown in FIG. 1 secured to the outside of the distal end 6 and the tip 7, the co-extrusion being critical to the present invention. The interior of the balloon 8 is in communication with at least one lumen (not shown in this FIG.) of the catheter tube 3. To form the tip 7 (and the portion of the catheter between the distal end 6 and the tip 7 to support the balloon 8) a portion of the catheter tube 3 is cut away so that only the lumen that houses an internal guide wire 14 remains (as shown in dotted lines within the balloon 8).

Extending through the interior of the tube 3 are a plurality of lumens (shown in FIGS. 3 and 4) which can serve a variety of functions, for example, housing the guide wire 14, inserting materials into the blood stream or inflating or deflating the balloon. Except for the balloon 8, all of the various components perform functions which are generally appreciated and known in the art.

To use, the catheter 1 (as shown in FIG. 2) is inserted into the cardiovascular system until the co-extruded balloon 8 is located at the site of an occlusion. At this stage, the balloon 8 is typically folded and collapsed and has an external diameter less than the inflated diameter, as can be seen by a comparison of FIGS. 1 and 2. Once the balloon 8 is maneuvered to the location of the occlusion, a pressurizing fluid is inserted at the proximal end 5 of the catheter tube 3 for inflation of the balloon 8. The fluid unfolds the balloon 8 until it presents a relatively smooth expanded profile for imparting forces that are radially outwardly directed at the desired site within the body in order to achieve the desired result of lesion dilation, restriction reduction or similar treatment.

Inserting the catheter 1 in an artery requires that the tube 3 be of a semi-flexible material. Tube 3 preferably is composed of a polyolefin copolymer, for example a conventional high density polyethylene. The diameter of the tubing is between about 12 and 16 French and may be coated on the inside and outside surfaces with, for example, a silicone based material to promote slippage in an aqueous environment.

As seen in FIGS. 3 and 4, the co-extruded balloon 8 results in a laminated construction. The laminates of the construction include a main structural layer 8B which is generally between about 0.2 and 2.5 mil. or thicker, and formed of one or more biaxially oriented polymers such as polyamides, polyesters, polycarbonates and their copolymers. Co-extruded with and bonded to the structural layer 8B is an inner layer SC of heat bondable polyolefin such as Plexar. Plexar is an anhydride-modified polyethylene and a trademarked product sold by Quantum Chemical Corporation of Cincinnati, Ohio. The heat bondable layer 8C is attached directly to the distal end 6 of catheter tube 3 and is secured to the balloon 8 by a heat seal joint 11. A similar joint 11 is formed between the balloon 8 and the catheter tip 7.

The heat bondable layer 8C is co-extruded with the structural layer 8B and has a thickness of between about 0.5 and 1.0 mil. Preferably, two heat bondable layers are co-extruded with the structural layer 8B. The inner layer 8B serves as a mechanism to provide a heat seal joint 10 between the distal end 6 of the catheter tube 3 and the structural layer 8B of the balloon 8. When two layers are co-extruded with the structural layer 8B, the inner layer 8C forms the heat bondable layer and the outer layer 8A forms a protective sheath for the main structural layer 8B. When polyamides such as Nylon are used as the structural layer 8B, Plexar can be used as the heat bonding layer 8C. The outer layer 8A can be formed of the same material and provide for softness for non-traumatic passing through vessels and good pin hole resistance.

An alternative to the construction shown in FIG. 1. another construction is to dispose a balloon formed of a base structural layer 8B of polyethylene terapthalate and an outer layer 8A of polyethylene around the distal end 6 of the catheter tube 3 and then place a sleeve 20 formed of heat bonding layer 20C of high density polyethylene on a base layer 20B of Nylon over the end of the balloon 8 whereby the polyethylene of the balloon seals to the polyethylene of the sleeve and the Nylon seals to the catheter 3. In cases where additional strength is needed, an innermost layer can be formed of high density polyethylene and an outermost layer is formed of Nylon with Plexar sandwiched therebetween.

It has been found that where strength, abrasion resistance and/or "feel" are important in medical balloons, that a co-extrusion which includes Selar resin can be used to provide for these characteristics. The Selar can be used by itself as the inner and/or outer layer or it can be blended with polyethylene terapthalate. Tests of a 1.6 mil. thick balloon with a Selar outer layer (a 50/50 blend of Selar and polyethylene terapthalate) were conducted by rubbing a balloon inflated to 6 atm. and rubbing it back and forth over medium grade emery cloth until failure. The balloons with Selar or 50/50 blend layers exceeded 200 cycles while a 1.8 mil. thick polyethylene terapthalate balloon failed in 87 cycles. Selar is a toughened grade of polyethylene terapthalate and it can be co-extruded with the base structural layers herein disclosed according to known techniques.

Referring to FIGS. 3 and 4, the interior of the co-extruded balloon 8 is shown in cross section. In FIG. 3, the balloon is shown in its distended or inflated condition whereas in FIG. 4 the balloon is shown in its deflated or folded condition. The balloon 8 can typically have an outer diameter that can be on the order of roughly three to six and even more times the outer diameter of the catheter tube 3. Pressurized fluids used to inflate the balloon include those conventionally used in the art, such as the well known aqueous solutions if they do not pose a problem of leaving residual fluids or chemically reacting with the balloon. Such fluids are introduced into the balloon 8 and removed therefrom through a lumen $L^1$ which is in fluid flow relationship with the interior thereof. Venting of gasses initially trapped in the catheter and the balloon prior to introduction of the inflation fluids is accomplished by expelling them through a second lumen $L^2$ also formed in the interior of the catheter tube 3. Preferably, lumen $L^1$ and $L^2$ are cut off at joint 10 so as to leave only a third lumen $L^3$.

The third lumen $L^3$ houses a guide wire 14 that passes through the balloon 8 and the tip 7. The third lumen $L^3$ is different then the other two lumens, $L^1$ and $L^2$, in that it extends entirely through the balloon 8 from the distal end 6 to the tip 7 so as to sheath the guide wire. In some embodiments, it may be desirable to combine the functions of lumens, $L^1$ and $L^2$, to only have a single lumen for inflating or deflating the balloon. Lastly, the lumen defined by $L^3$ provides for a housing for a guide wire 14 which is removably housed in it. Guide wire 14 passes through the entire length of the catheter 3 and through the balloon 8 (while preferably sheathed in lumen $L^3$) and thence into an axial bore (not shown) in tip 7 to emerge from the end of tip 7 (as shown in FIGS. 2 and 3).

Each of the lumens $L^1$, $L^2$ and $L^3$ is formed by walls 15 and 16 that are extruded as the catheter tube is extruded from an extrusion machine, as is well known in the art. The thickness of the walls 15 and 16 can be between 0.5 and 10 mil., as is well known.

As shown in FIG. 4, the diameter of the folded balloon 8 is substantially the same or less than the diameter of the catheter tube 3 so as to provide for easy passage of the catheter through blood vessels. The extruded tubing 3 has a nominal wall thickness that generally is on the order of six to twelve times the desired wall thickness of the balloon 8.

To form the co-extruded balloons, the materials initially-are melted separately in extrusion machines. When melted, the materials are separately forced into an extrusion head and extruded so that they are forced out as a plurality of layers in the form of a single tube which critically forms the balloon of the present invention. A Nylon-Plexar or polyethylene-polyethylene terapthalate balloon may be formed by taking a six inch length of the three layered tubing which is to be manufactured into a balloon and placing it in a holding fixture. The left hand end of the tube is attached to a Touhy Borst adapter. The right hand end of the tube is heat sealed to temporarily prevent pressurized air from escaping. The right hand end is attached to a tension line which is pulled for the force of a least 150 grams (for a 3.0 mm. diameter balloon). The tubing is heated under a pressure of between about 100 and 400 psi to about 210° F. for several seconds. Afterwards, the heated area is cooled and the support frame is spread apart slightly so as to expose a pre-determined section of tubing to permit the balloon area to be reheated to a temperature between about 210° and 220° F. to permit the balloon to be expanded to a desired diameter under pressure for about 35 seconds. The pressure is then stopped and the deflectors are slid to the ends of the balloon and the balloon is heated for a third time to about 310° F. to heat set the balloon and biaxially orient the polymeric matrix. This third heating prevents the balloon layers from flaking and prevents the balloon from expanding beyond the size at which it will set during the heat setting period. The heat setting takes about 8 seconds.

For a Nylon-Plexar balloon, the deflectors from the tubes are then removed and another unheated tube is mounted into the fixture. The catheter tube is slid inside the balloon so that it engages the heat bondable polyethylene layer. The balloon is bonded to the polyethylene shaft by heat bonding in a temperature of about 310° F. which is long enough to the melt the polyethylene end and the inner layer of the polyethylene together.

It is quite important to recognize that the heat treatment steps as described herein essentially prevent the delamination of the heat bondable layers 8C and 8A from the main structural layer 8B as is required when a laminated construction is used as a catheter. Flaking and delamination is not a problem, however, with polyethylene terapthalate and Selar layers.

While it is apparent that modifications and changes may be made within the spirit and scope of the present invention, it is intended, however, only to be limited by the scope of the appended claims.

What is claimed is:

1. A method of forming a balloon for medical purposes, said method comprising;

co-extruding in a tubular shape a base structural layer of a member selected from the group consisting of polyamides, polycarbonates, polyesters and copolymers thereof and a heat sealable layer selected from the group consisting of polyethylene and copolymers thereof;

biaxially orienting said base structural layer by inflating said tube with a gas to a predetermined central diameter greater than the initial diameter of the tubular shape and simultaneously heating the inflated tube to a temperature sufficient to biaxially orient said base structural layer;

cooling the inflated tubular member;

elevating the temperature of the inflated tube for a second time to said biaxially orienting temperature;

allowing the twice-heated tube to cool and withdrawing the gas whereby the tubular member will assume a generally tubular shape and said,main structural layer will remain biaxially orientated and said heat sealable layer will not be biaxially orientated.

* * * * *